US010613513B2

(12) United States Patent
Livingston

(10) Patent No.: US 10,613,513 B2
(45) Date of Patent: *Apr. 7, 2020

(54) SYSTEMS AND METHODS FOR MODIFYING MATERIAL SUBSTRATES

(71) Applicant: The Aerospace Corporation, El Segundo, CA (US)

(72) Inventor: Frank Edward Livingston, Redondo Beach, CA (US)

(73) Assignee: The Aerospace Corporation, El Segundo, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 15/469,132

(22) Filed: Mar. 24, 2017

(65) Prior Publication Data

US 2017/0199512 A1 Jul. 13, 2017

Related U.S. Application Data

(63) Continuation-in-part of application No. 14/163,712, filed on Jan. 24, 2014, now Pat. No. 10,228,666, (Continued)

(51) Int. Cl.
*G05B 19/37* (2006.01)
*G05B 19/4093* (2006.01)
(Continued)

(52) U.S. Cl.
CPC .... *G05B 19/40937* (2013.01); *A61F 2/30771* (2013.01); *G05B 15/02* (2013.01);
(Continued)

(58) Field of Classification Search
CPC .............. B23K 26/0622; B23K 26/04; B23K 26/0626; B23K 26/0006; B23K 26/06;
(Continued)

(56) References Cited

U.S. PATENT DOCUMENTS 5,170,403 A * 12/1992 Mayer ................ H01S 5/06832
372/26
5,233,175 A * 8/1993 Latta .................... G11B 7/1356
250/205
(Continued)

OTHER PUBLICATIONS

Livingston et al., "Chapter 9: Laser Processing Architecture for Improved Material Processing"; Laser Processing of Materials: Fundamentals, Applications, and Developments, P. Schaaf, Ed., Springer Series Materials Science, Springer-Verlag, Berlin; (2010), pp. 189-224.
(Continued)

*Primary Examiner* — Darrin D Dunn
(74) *Attorney, Agent, or Firm* — Manita Rawat; Duane Morris LLP

(57) ABSTRACT

A system includes a computing device that generates at least one process script for the modification to a material substrate and at least one pattern script that corresponds to the process script. The computing device also merges the process script with the pattern script and generates a plurality of command signals that are based on the merged process and pattern scripts. An energy source generates a plurality of light beams based on the generated command signal(s). At least one modulating component modulates the generated light beams based on generated command signal(s). A waveform apparatus generates at least one waveform signal to customize the generated light beams based on the generated command signal(s). A motion control apparatus controls at least one parameter of the light beams based on the generated command signal(s).

17 Claims, 4 Drawing Sheets

Related U.S. Application Data which is a continuation-in-part of application No. 13/767,055, filed on Feb. 14, 2013, now Pat. No. 8,679,189.

(60) Provisional application No. 61/763,223, filed on Feb. 11, 2013.

(51) Int. Cl.
*G05B 15/02* (2006.01)
*A61F 2/30* (2006.01)

(52) U.S. Cl.
CPC ........... *A61F 2002/3097* (2013.01); *G05B 2219/36032* (2013.01); *G05B 2219/37415* (2013.01)

(58) Field of Classification Search
CPC ... H01S 3/1305; H01S 5/06216; H01S 5/0683
See application file for complete search history.

(56) References Cited

U.S. PATENT DOCUMENTS

| | | | |
|---|---|---|---|
| 6,423,935 B1* | 7/2002 | Hackel | G06K 1/126 219/121.85 |
| 6,489,985 B1* | 12/2002 | Brodsky | B23K 26/032 347/237 |
| 6,783,920 B2 | 8/2004 | Livingston et al. | |
| 7,248,940 B2 | 7/2007 | Neumann et al. | |
| 7,526,357 B2* | 4/2009 | Livingston | B23K 26/0626 438/689 |
| 7,742,511 B2* | 6/2010 | Murison | H01S 3/06758 372/26 |
| 8,378,258 B2* | 2/2013 | Sercel | B23K 26/0732 219/121.69 |
| 8,679,189 B1 | 3/2014 | Ganey et al. | |
| 8,723,074 B2 | 5/2014 | Sercel et al. | |
| 8,772,671 B2 | 7/2014 | Broude et al. | |
| 8,785,813 B2 | 7/2014 | Shah et al. | |
| 8,835,798 B2 | 9/2014 | Rumsby | |
| 9,018,562 B2 | 4/2015 | Dantus | |
| 9,104,194 B2 | 8/2015 | Mori et al. | |
| 9,358,636 B2 | 6/2016 | Hammann et al. | |
| 9,486,877 B2* | 11/2016 | Unrath | B23K 26/03 |
| 10,228,666 B2 | 3/2019 | Livingston et al. | |
| 2002/0024714 A1* | 2/2002 | Sandstrom | G02B 26/0833 359/290 |
| 2002/0044197 A1* | 4/2002 | Furumiya | B41J 3/445 347/247 |
| 2002/0072823 A1* | 6/2002 | Belanger | G05B 19/4142 700/159 |
| 2002/0185610 A1* | 12/2002 | Stern | C12Q 1/6834 250/458.1 |
| 2003/0071994 A1 | 4/2003 | Borden et al. | |
| 2004/0031779 A1* | 2/2004 | Cahill | B23K 26/04 219/121.83 |
| 2004/0254665 A1 | 12/2004 | Fink et al. | |
| 2005/0005642 A1 | 1/2005 | Kaplan et al. | |
| 2005/0018738 A1* | 1/2005 | Duan | B41J 3/4071 372/55 |
| 2005/0029965 A1* | 2/2005 | Yamaguchi | G02B 26/12 315/291 |
| 2005/0058190 A1* | 3/2005 | Sato | G01R 31/3171 375/224 |
| 2005/0103760 A1 | 5/2005 | Kaplan et al. | |
| 2006/0028655 A1* | 2/2006 | Cordingley | B23K 26/032 356/614 |
| 2006/0068334 A1* | 3/2006 | Sandstrom | G03F 7/70283 430/322 |
| 2006/0088074 A1* | 4/2006 | Johnstone | H01S 3/2383 372/70 |
| 2006/0097430 A1 | 5/2006 | Xiaochun et al. | |
| 2006/0102601 A1* | 5/2006 | Shirk | B23K 26/03 219/121.68 |
| 2006/0102608 A1 | 5/2006 | Katsuta et al. | |
| 2006/0126477 A1* | 6/2006 | Livingston | B23K 26/0626 369/116 |
| 2006/0181997 A1* | 8/2006 | Tanase | G11B 7/0062 369/59.11 |
| 2006/0191884 A1* | 8/2006 | Johnson | B23K 26/04 219/121.85 |
| 2008/0043220 A1 | 2/2008 | Kaplan et al. | |
| 2008/0232817 A1* | 9/2008 | Futami | B82Y 20/00 398/160 |
| 2009/0067455 A1* | 3/2009 | Murison | H01S 3/06758 372/20 |
| 2009/0188901 A1 | 7/2009 | Dantus | |
| 2010/0141729 A1 | 6/2010 | Petsch et al. | |
| 2010/0197116 A1 | 8/2010 | Shah et al. | |
| 2010/0260029 A1* | 10/2010 | Kurihara | G11B 7/1267 369/100 |
| 2011/0013175 A1 | 1/2011 | Davis et al. | |
| 2011/0024400 A1 | 2/2011 | Rumsby | |
| 2011/0026552 A1* | 2/2011 | Iwasaki | H01S 5/0683 372/38.01 |
| 2011/0182319 A1* | 7/2011 | Hua | H01S 3/134 372/55 |
| 2011/0267593 A1 | 11/2011 | Hsieh et al. | |
| 2011/0272575 A1* | 11/2011 | Kim | B41J 2/04563 250/288 |
| 2012/0002687 A1* | 1/2012 | Ershov | H01S 3/225 372/20 |
| 2012/0015318 A1 | 1/2012 | Kasenbacher | |
| 2012/0138586 A1 | 6/2012 | Webster et al. | |
| 2012/0241427 A1* | 9/2012 | Maltsev | B23K 26/0732 219/121.85 |
| 2012/0276754 A1* | 11/2012 | Cordingley | B23K 26/032 438/795 |
| 2012/0328905 A1 | 12/2012 | Guo et al. | |
| 2013/0010349 A1* | 1/2013 | Cordingley | G02F 1/33 359/305 |
| 2013/0066447 A1 | 3/2013 | Baierl-Moehler et al. | |
| 2013/0094529 A1* | 4/2013 | Wakabayashi | H01S 3/0057 372/27 |
| 2013/0101251 A1* | 4/2013 | Kawamura | G02B 6/12 385/14 |
| 2013/0113510 A1* | 5/2013 | Kasapi | G01R 31/308 324/754.23 |
| 2013/0120740 A1 | 5/2013 | Schonleber | |
| 2013/0215916 A1* | 8/2013 | Kakizaki | H01S 3/10092 372/21 |
| 2013/0328504 A1* | 12/2013 | Yavor | H05B 33/0815 315/307 |
| 2014/0098410 A1* | 4/2014 | Cordingley | G02F 1/33 359/307 |
| 2014/0110384 A1* | 4/2014 | Kleinert | B23K 26/082 219/121.66 |
| 2014/0228991 A1 | 8/2014 | Livingston et al. | |
| 2014/0263223 A1* | 9/2014 | Unrath | B23K 26/032 219/121.81 |
| 2015/0025667 A1 | 1/2015 | Shindo et al. | |
| 2015/0336208 A1* | 11/2015 | Sokol | B23K 26/356 219/121.61 |
| 2016/0167164 A9* | 6/2016 | Rosario | B23K 26/0006 347/225 |
| 2018/0356797 A1* | 12/2018 | Livingston | G05B 19/4155 |

OTHER PUBLICATIONS

M.E. Lines and A.M. Glass, "Chapeter 8: Oxygen Octahedra"; Principles and Applications of Ferroelectrics and Related Materials; Claredon Press, Oxford, 1977, pp. 241-246.

J. Wolff, Das Gesetz der Transformation der Knochen, Verlag bon Aug. Hirschwald, Berlin, Germany, 1892, (ISBN) 978-3-86805-648-8.

Wilson et al., "Life on Earth", Sinauer Association, Stamford, CT 1973.

J. Brannon, J. Greer, and H. Helvajian, "Laser Processing for Microengineering Applications." In: Microengineering Aerospace

(56) References Cited

OTHER PUBLICATIONS

Systems, ed. by H. Helvajian, The Aerospace Press, El Segundo, CA 1999.
A.J. Ikushima, T. Fujiwara, and K. Saito, J. Appl. Phys. 88, 1201, (2000).
H. Becker, M. Arundell, A. Harnisch, and D. Hulsenberg, Sens. Actuators B 86, 271 (2002).
M. Toner, and H. Buettner, Biotechnol. Prog. 14, 355 (1998).
S.D. Stookey, Indust. Eng. Chem. 51, 805 (1959).
T. Tashiro, and M. Wada, "Glass-Ceramics Crystallized with Zirconia. In: Advances in Glass Technology", Plenum Press, New York, NY 1963.
A.G. Pincus, "Application of Glass-Ceramics." In: Advances in Nucleation and Crystallization in Glasses, ed. by L.L. Hench, S.W. Frieman, The American Ceramic Society, Columbus, OH 1971.
S.D. Stookey, Indust. Eng. Chem. 45, 115 (1953).
S.D. Stookey, Indust. Eng. Chem. 41, 856 (1949).
P.J. Brock, M.D. Levenson, J.M. Zavislan, and J.R. Lyerla, J. Vac. Sci. Technol. B9, 3155 (1991).
T.R. Dietrich, W. Ehrfeld, M. Lacher, M. Kramer, and B. Speit, Microelectron. Eng. 30, 497 (1996).
Livingston et al., "Photophysical Processes that Lead to Ablation-Free Microfabrication in Glass-Ceramic Materials." In: 3D Laser Microfabrication, ed. by H. Misawa, S. Juodkazis, Wiley-VCH, Weinheim, 2006 and references therein.
Y. Cheng, K. Sugioka, M. Masuda, K. Shihoyama, K Toyoda, and K. Midorikawa, Proc. SPIE 5063, 103 (2003).
W.W. Hansen, S.W. Janson, and H. Helvajian, Proc. SPIE 2991, 104 (1997).
J. Kim, H. Berberoglu; and X. Xu, J. Microlith. Microfab. Microsyst. 3, 478 (2004).
F.E. Livingston and H. Helvajian, Proc. SPIE 4830, 189 (2003).
F.E. Livingston and H. Helvajian, Appl. Phys. A 81, 1569 (2005).
M. Masuda, K Sugioka, Y. Cheng, T. Hongo, K. Shihoyama, H. Takai, I. Miyamoto, and K. Midorikawa, Appl. Phys, A 78, 1029 (2004).
K. Sugioka, M. Masuda, T. Hongo, Y. Cheng, K. Shihoyama, and K. Midorikawa, Appl. Phys, A 79, 815 (2004).
S.W. Janson, A. Huang, W.W. Hansen, and H. Helvajian, AIAA paper 2004-6701, Conference on Micro-Nano-Technologies, Monterey, CA 2004.
V. Arbuzov, J. Non-Cryst. Solids 253, 37 (1999).
J.S. Stroud, J. Chem. Phys. 37, 836 (1962).
M. Talkenberg, E.W. Kreutz, A. Horn, M. Jacquorie, and R. Poprawe, Proc. SPIE 4637, 258 (2002).
F.E. Livingston, W.W. Hansen, A. Huang, and H. Helvajian, Proc. SPIE 4637, 404 (2002).
F.E Livingston, P.M. Adams, and H. Helvajian, Appl. Phys. A 89, 97 (2007).

* cited by examiner

SYSTEMS AND METHODS FOR MODIFYING MATERIAL SUBSTRATES

RELATED AND CO-PENDING APPLICATION

This application is a continuation-in-part of and claims priority to co-pending U.S. patent application Ser. No. 14/163,712 entitled MATERIAL MODIFICATION ASSEMBLY AND METHOD FOR USE IN THE MODIFICATION OF MATERIAL SUBSTRATES filed Jan. 24, 2014, which is a continuation-in-part of and claims priority to U.S. patent application Ser. No. 13/767,055 entitled BONE GROWTH ENHANCING IMPLANT filed Feb. 14, 2013 and issued as U.S. Pat. No. 8,679,189 on Mar. 25, 2014, which claims the benefit of U.S. Provisional Application 61/763,223, filed Feb. 11, 2013, the disclosures of which are incorporated herein by reference in its entirety.

BACKGROUND

At least some known material substrates, such as skeletal implant structures and related interbody devices, can be used for various applications ranging from surgical repairs and orthopedic restoration to regenerative medicine and pain mitigation therapies. At least some known material substrates, such as implants, include passive structural systems whose physical and chemical properties are intended to align with, for example, human bone, to enable mechanical integrity and biocompatibility for long-term acceptance into the skeletal structure. At least some known approaches or techniques are used to facilitate integration of the material substrate, such as the implant, into the body. For example, mechanical and chemical modalities can be used, wherein mechanical manipulation and chemical treatments are used to affect surface structure and roughness prior to implantation. Electrical modalities, such as nascent electrochemical stimuli, can be used to govern cellular activity and function in the human body for the implant. Other techniques, such as the use of direct current ("DC"), inductive coupling ("IC"), capacitive coupling ("CC"), and low-intensity pulsed ultrasound ("LIPUS"), can also be used to facilitate integration of the material substrate into the body.

In spite of these techniques, such material substrates, such as implants, can require external intervention and therapeutic options for enhancing, for example, tissue growth and bone fusion, for improving fixation and stability. However, the restorative devices and methods can be invasive and, in some circumstances, can require additional surgery, bulky power sources, and frequent maintenance. Moreover, the lack of customization and genetic design, along with patient non-compliance, may further amplify the challenges associated with current implant approaches.

BRIEF DESCRIPTION

The embodiments described herein enable an approach to create and/or modify material substrates, such as implants, with built-in electromechanical properties that are encoded for response and functionality, and appropriately patterned for form and function. For example, in one embodiment, a system for modifying at least one material substrate is provided. The system includes a computing device that is configured to generate at least one process script for the modification to the material substrate and to generate at least one pattern script that corresponds to the process script, for the modification to the material substrate. The computing device is also configured to merge the generated process script with the corresponding generated pattern script and to generate a plurality of command signals that are based on the merged generated process script and the corresponding generated pattern script. An energy source is configured to couple to the computing device, wherein the energy source is further configured to generate a plurality of light beams based on at least one of the generated command signals. At least one modulating component is configured to couple to the computing device and the energy source, wherein the modulating component is further configured to modulate the generated light beams based on at least one of the generated command signals. A waveform apparatus is configured to couple to the computing device, the energy source, and the modulating component. The waveform apparatus is further configured to generate at least one waveform signal to customize the generated light beams based on at least one of the generated command signals. A motion control apparatus is configured to couple to the computing device, the at least one modulating component, the energy source, and the waveform apparatus. The motion control apparatus is further configured to control at least one parameter of the light beams based on at least one of the generated command signals.

In another embodiment, a method for modifying at least one material substrate is provided. At least one process script is generated, via a computing device, to modify the material substrate. At least one pattern script is generated that corresponds to the process script, via the computing device, to modify the material substrate. The generated process script is merged with the corresponding generated pattern script. A plurality of command signals are generated that are based on the merged generated process script and the corresponding generated pattern script. A plurality of light beams are generated, via an energy source, based on at least one of the generated command signals. The generated light beams are modulated, via a modulating component, based on at least one of the generated command signals. At least one waveform signal is generated to customize the generated light beams, via a waveform apparatus, based on at least one of the generated command signals. At least one parameter of the light beams is controlled, via a motion control apparatus, based on at least one of the generated command signals.

In yet other embodiments, a system is provided. The system includes at least one material substrate. A computing device is positioned proximate to the material substrate, wherein the computing device is configured to generate at least one process script for the modification to at least a surface of the material substrate and to generate at least one pattern script that corresponds to the process script, for the modification to at least the surface of the material substrate. The computing device is further configured to merge the generated process script with the corresponding generated pattern script to generate a plurality of command signals that are based on the merged generated process script and the corresponding generated pattern script. An energy source is configured to couple to the computing device, wherein the energy source is further configured to generate a plurality of light beams based on at least one of the generated command signals. At least one modulating component is configured to couple to the computing device and the energy source, wherein the modulating component is further configured to modulate the generated light beams based on at least one of the generated command signals. A waveform apparatus is configured to couple to the computing device, the energy source, and the modulating component, wherein the waveform apparatus is further configured to generate at least one waveform signal to customize the generated light beams based on at least one of the generated command signals. A motion control apparatus is configured to couple to the computing device, the modulating component, the energy source, and the waveform apparatus, wherein the motion control apparatus is further configured to control at least one parameter of the light beams based on at least one of the generated command signals.

DETAILED DESCRIPTION

The embodiments described herein enable the fabrication of material substrates, such as bioactive implants and interbody devices, that control human cellular chemistry via electromechanical pathways and physics-based inductions that enable guiding the body's physiology to facilitate bone cell activity for improved tissue attachment, bone growth and fusions. The embodiments described herein include, for example, the use of laser genotype pulse modulation techniques to induce site-selective phase conversion and ferroelectric, piezoelectric and pyroelectric activation in biomaterials for creating complex electromechanical architectures and networks that are superimposed on the implant geometry. For example, ferro-, piezo- and pyroelectric domains that suit implant dimension, function, and location can be defined. Electrochemical domains can also be homogenous or inhomogeneous (i.e., gradient), and tailored for direct response to natural physiological forces or controlled via external wireless stimulation for closed-loop biofeedback.

Figure 1:
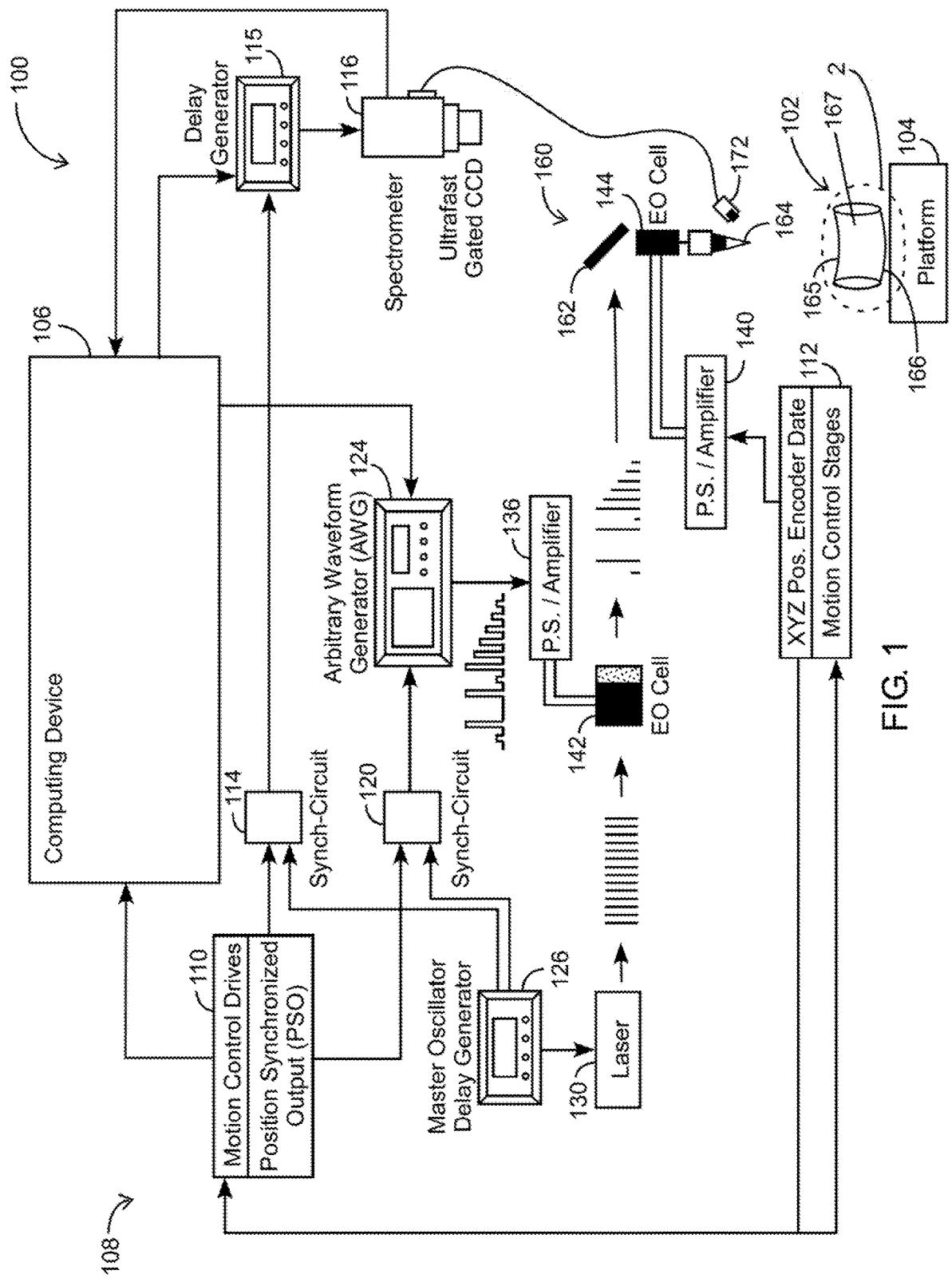
FIG. 1 is block diagram of an exemplary system that includes a material substrate in accordance with some embodiments of the present disclosure.

FIG. 1 illustrates an exemplary system 100. In some embodiments, system 100 can be a bone growth enhancing system that is configured to design and create, for example, a bone implant device (not shown) that can be used on a mammal, such as a human. For example, in some embodiments, system 100 includes a material substrate 102 that is positioned on a platform 104, such as a surgical table, wherein material substrate 102 can be modified to form, for example, the bone implant device. It should be noted that the present disclosure is not limited to bone growth enhancing systems and one of ordinary skill in the art will appreciate that the current disclosure may be used in connection with other types of systems that are used to modify various types of material substrates. For example, in some embodiments, system 100 can be a power system that is used to modify, such as texturize, a metal component (not shown), such as a turbine.

In some embodiments, system 100 includes a computing device 106 that can be, for example, a desktop computer, laptop, mobile device, tablet, thin client, or other device having a communications interface (not shown) that can communicate with other components of system 100, as explained in more detail below with respect to FIG. 2. For example, in some embodiments, computing device 106 is coupled to a motion control apparatus 108 via a suitable connection, including, but not limited to, an electrical conductor, a low-level serial data connection, such as Recommended Standard (RS) 232 or RS-485, a high-level serial data connection, such as USB, a field bus, a PROFIBUS®, or Institute of Electrical and Electronics Engineers (IEEE) 1394 (a/k/a FIREWIRE), a parallel data connection, such as IEEE 1284 or IEEE 488, a short-range wireless communication channel such as BLUETOOTH, and/or a private (e.g., inaccessible outside system 100) network connection, whether wired or wireless. IEEE is a registered trademark of the Institute of Electrical and Electronics Engineers, Inc., of New York, N.Y. BLUETOOTH is a registered trademark of Bluetooth SIG, Inc. of Kirkland, Wash. PROFIBUS is a registered trademark of Profibus Trade Organization of Scottsdale, Ariz. It should be noted that, as used herein, the term "couple" is not limited to a direct mechanical, thermal, communication, and/or an electrical connection between components, but may also include an indirect mechanical, thermal, communication and/or electrical connection between multiple components.

In some embodiments, motion control apparatus 108 includes motion control drives 110 and motion control stages 112. Motion control system 108 is coupled to a first synch circuit 114 that is coupled to a delay generator 115 and to a detection device, such as a spectrometer 116. In some embodiments, first synch circuit 114 can be any suitable commercially available circuit that is programmed to control the timing of signals being channeled through system 100 based on information received from computing device 106. In some embodiments, spectrometer 116 can be any suitable commercially available spectrometer, detection device, sensing element or similar monitoring instrument.

In some embodiments, motion control apparatus 108 is coupled to a second synch circuit 120 that is coupled to a waveform generator 124 and a master oscillator delay generator 126. In some embodiments, waveform generator 124 can be any suitable commercially available arbitrary waveform generator. Second synch circuit 120 can also be any suitable commercially available circuit that is programmed to control the timing of signals. In some embodiments, an energy source, such as a laser 130, is coupled to master oscillator delay generator 126. In some embodiments, laser 130 can be any suitable laser that is configured to generate a plurality of pulsed light beams. In some embodiments, other types of energy sources can be used instead of lasers, such as electron beams, x-rays, proton beams, and lamp and arc sources.

In some embodiments, waveform generator 124 is also coupled to an amplifier 136 and motion control apparatus 108 is coupled to an amplifier 140. In some embodiments, amplifiers 136 and 140 are each configured to alter any signals received therein. The signals can be altered according to a transfer function, such as to apply a gain factor to multiply the voltage or current or numerically digitized amplitude of the signals received therein to generate modified output signals, such as an amplified signals.

In some embodiments, system 100 also includes one or more modulating devices or components, such as a first electro-optic (EO) modulator cell 142 and a second EO modulator cell 144. First EO modulator cell 142 is coupled to amplifier 136 in some embodiments. Second EO modulator cell 144 is coupled to a an optical assembly 160 that includes an optical device, such as a lens or mirror 162, and a focusing conduit 164 to focus the light beams that go through lens 162 onto material substrate 102. For example, in some embodiments, the light beams are focused onto at least a portion of top exterior surface 165, bottom exterior surface 166, and/or side exterior surface 167. In some embodiments, when other types of energy sources are used instead of laser 130, they can be modulated by devices other than EO cell modulators 142 and 144 to generate scripts of the other energy types, such as electron scripts, proton scripts, x-ray scripts etc.

Spectrometer 116 is positioned proximate to material substrate 102 such that a sensing element or a transducer 172 of spectrometer 116 is coupled to at least a portion of material substrate 102. Spectrometer 116 is also coupled to computing device 106. In some embodiments, spectrometer 116 is configured to detect various aspects of the modification being performed on material substrate 102.

During operation of system 100, photons are administered in discrete and pre-defined packets, synchronized with the pattern and biogeometry, to create a tapestry or mosaic of materials states on material substrate 102 with different phases, compositions, and functionalities. For example, as explained in more detail below with respect to FIGS. 2-4, computing device 106 is configured generate at least one process script for the modification to material substrate 102 and to generate at least one pattern script that corresponds to the process script, for the modification to material substrate 102. Computing device 106 merges the generated process script with the corresponding generated pattern script and generates a plurality of command signals that are based on the merged process script and pattern script. Laser 130 receives at least one of the generated command signals and laser 130 generates a plurality of light beams based on the received command signal. In addition, EO modulator cells 142 and 144 can also receive at least one of the generated command signals and are configured to modulate the generated light beams based on the received command signal. Waveform generator 124 is also configured to receive at least one of the generated command signals and to generate at least one waveform signal to customize the generated light beams based on the received command signal. Motion control apparatus 108 receives at least one of the generated command signals and controls at least one parameter of the light beams based on the command signal.

Figure 2:
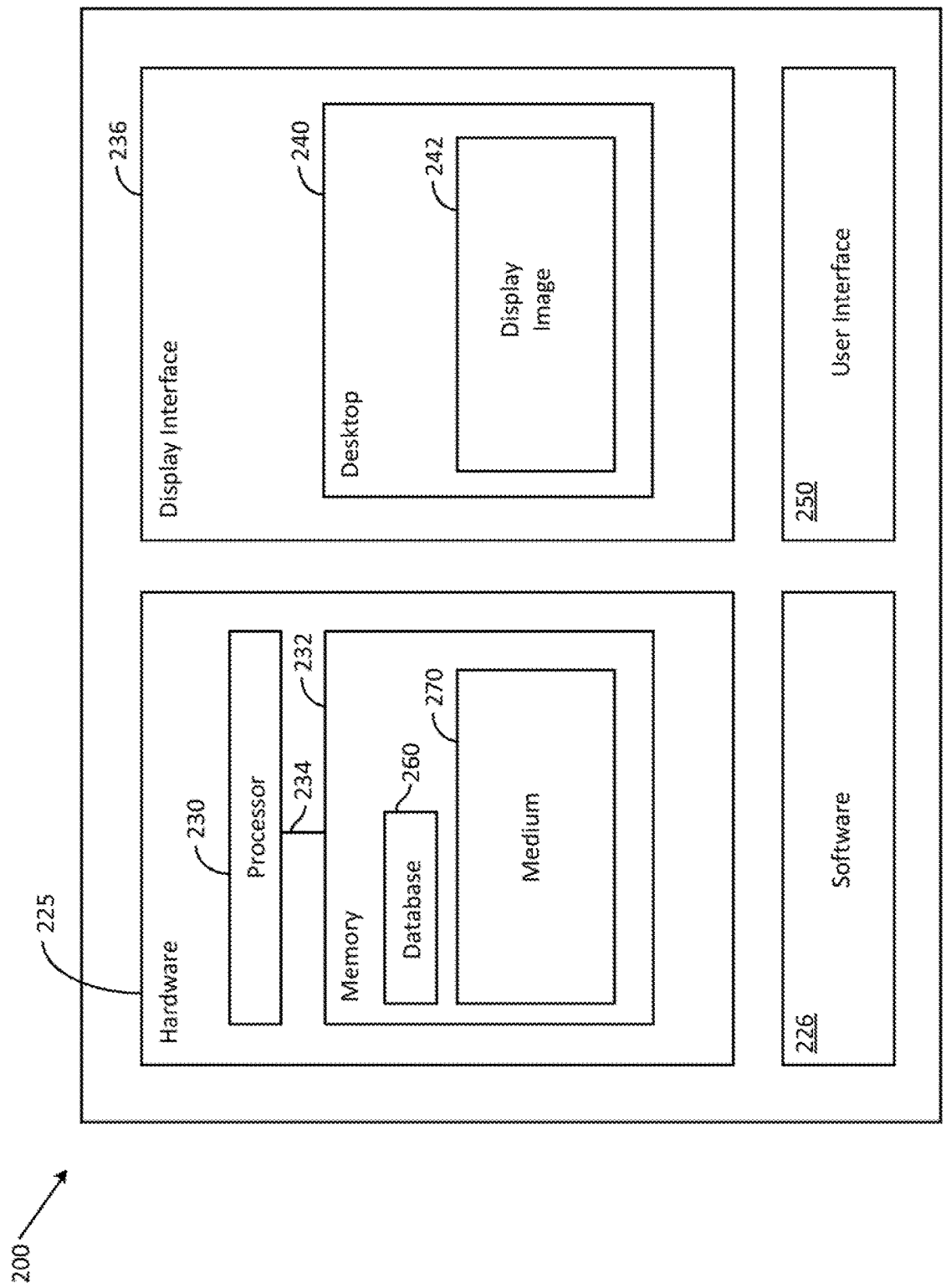
FIG. 2 is a block diagram of an exemplary computing device that can be used with the system shown in FIG. 1, in accordance with some embodiments of the present disclosure.
Figure 3:
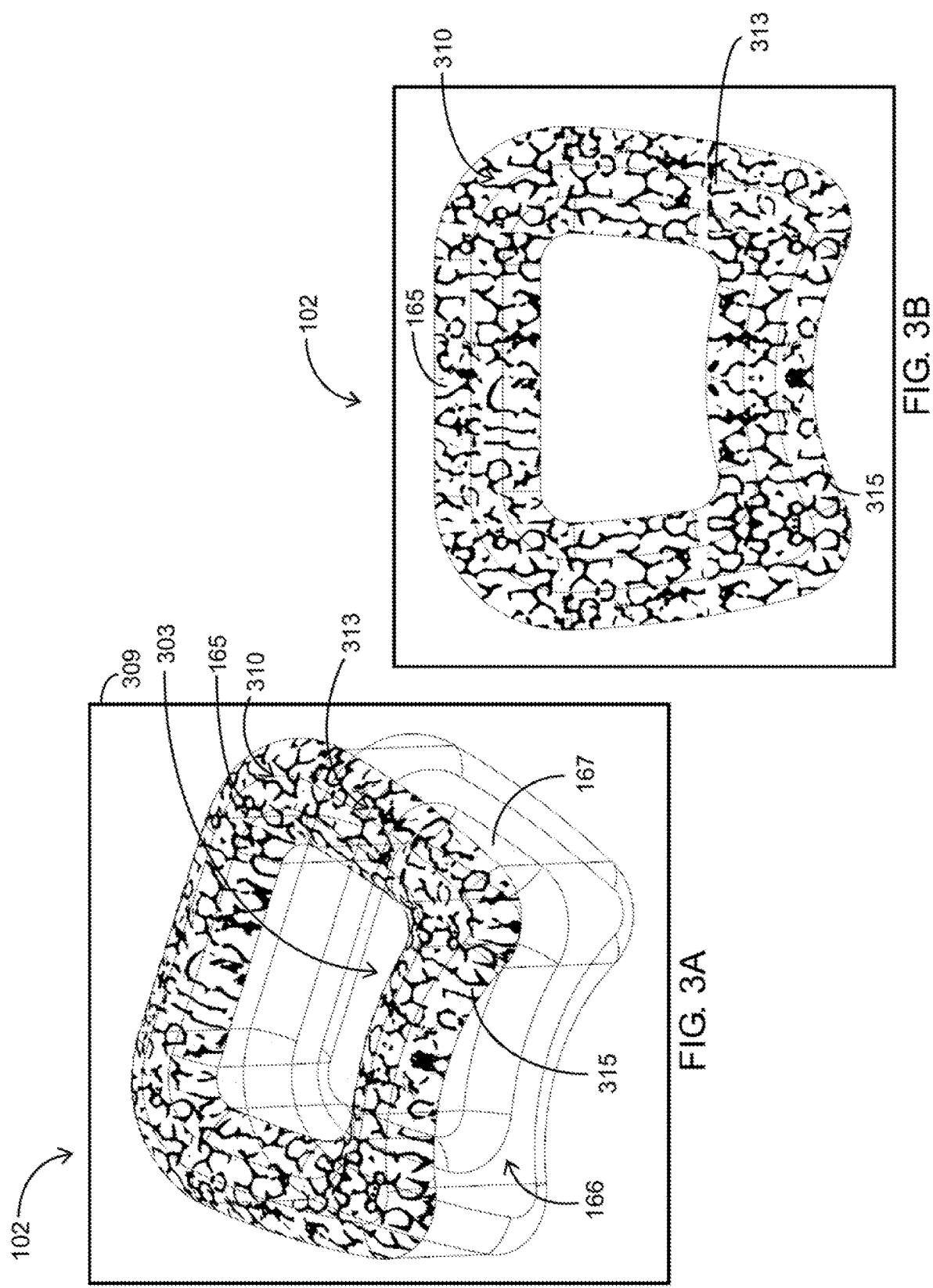
FIG. 3A is a perspective view of the material substrate shown in FIG. 1 and taken from area 1 and taken from area 1, in accordance with some embodiments of the present disclosure.
FIG. 3B is a top view of the material substrate shown in FIG. 3A, in accordance with some embodiments of the present disclosure.

FIG. 2 is a block diagram of an exemplary computing device 200, which may be used to implement computing device 106 (FIG. 1). In some embodiments, computing device 200 includes a hardware unit 225 and software 226. Software 226 can run on hardware unit 225 such that various applications or programs can be executed on hardware unit 225 by way of software 226. In some embodiments, the functions of software 326 can be implemented directly in hardware unit 225, e.g., as a system-on-a-chip, firmware, field-programmable gate array ("FPGA"), etc. In some embodiments, hardware unit 225 includes one or more processors, such as processor 230. In some embodiments, processor 230 is an execution unit, or "core," on a microprocessor chip. In some embodiments, processor 230 may include a processing unit, such as, without limitation, an integrated circuit ("IC"), an ASIC, a microcomputer, a programmable logic controller ("PLC"), and/or any other programmable circuit. Alternatively, processor 230 may include multiple processing units (e.g., in a multi-core configuration). The above examples are exemplary only, and, thus, are not intended to limit in any way the definition and/or meaning of the term "processor."

Hardware unit 225 also includes a system memory 232 that is coupled to processor 230 via a system bus 234. Memory 232 can be a general volatile RAM. For example, hardware unit 225 can include a 32 bit microcomputer with 2 Mbit ROM and 64 Kbit RAM, and/or a few GB of RAM. Memory 232 can also be a ROM, a network interface (NIC), and/or other device(s).

In some embodiments, computing device 200 can also include at least one media output component or display interface 236 for use in presenting information to a user. Display interface 236 can be any component capable of conveying information to a user and may include, without limitation, a display device (not shown) (e.g., a liquid crystal display ("LCD"), an organic light emitting diode ("OLED") display, or an audio output device (e.g., a speaker or headphones)). In some embodiments, computing device 300 can output at least one desktop, such as desktop 240. Desktop 240 can be an interactive user environment provided by an operating system and/or applications running within computing device 200, and can include at least one screen or display image, such as display image 242. Desktop 240 can also accept input from a user in the form of device inputs, such as keyboard and mouse inputs. In some embodiments, desktop 240 can also accept simulated inputs, such as simulated keyboard and mouse inputs. In addition to user input and/or output, desktop 240 can send and receive device data, such as input and/or output for a FLASH memory device local to the user, or to a local printer.

In some embodiments, display image 242 can be presented to a user on computer displays of a remote terminal (not shown). For example, computing device 200 can be connected to one or more remote terminals (not shown) or servers (not shown) via a network (not shown), wherein the network can be the Internet, a local area network ("LAN"), a wide area network ("WAN"), a personal area network ("PAN"), or any combination thereof, and the network can transmit information between computing device 300 and the remote terminals or the servers, such that remote end users can access the information from computing device 200.

In some embodiments, computing device 200 includes an input or a user interface 250 for receiving input from a user. User interface 250 may include, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the media output component and the input interface. In some embodiments, mobile devices, such as tablets, can be used.

Computing device 200, in some embodiments, can include a database 260 within memory 232, such that various information can be stored within database 260. Alternatively, in some embodiments, database 260 can be included within a remote server (not shown) with file sharing capabilities, such that database 260 can be accessed by computing device 200 and/or remote end users. In some embodiments, a plurality of computer-executable instructions can be stored in memory 232, such as one or more computer-readable storage media 270 (only one being shown in FIG. 2). Computer storage medium 270 includes non-transitory media and may include volatile and nonvolatile, removable and non-removable mediums implemented in any method or technology for storage of information such as computer-readable instructions, data structures, program modules or other data. The instructions may be executed by processor 230 to perform various functions described herein, e.g., steps of the process shown in FIG. 4.

FIG. 3A illustrates a perspective view of material substrate 102 taken from area 1 (shown in FIG. 1) and FIG. 3B illustrates a top view of material substrate 102. Material substrate 102 has a substantially cylindrical shape and a channel 303 is defined therein such that channel 103 extends through top exterior surface 165 and bottom exterior surface 166 of material substrate 102. Side exterior surface 167 substantially circumscribes at least a portion of material substrate 102 such that top exterior surface 165, bottom exterior surface 166, and channel 303 are not enclosed or covered by side exterior surface 167. In some embodiments, channel 303 is defined by an interior surface 309. In some embodiments, side exterior surface 167 and interior surface 309 can be made of an organic carbon or hydrocarbon base material that is synthetically produced, such as a polymer of a plastic material or a ceramic composition. In some embodiments, top exterior surface 165 and bottom exterior surface 166 can be composed of any implantable grade material, such as a polyether ether ketone (PEEK), polyether ketone ketone (PEKK), polyethylene, ultra high molecular weight polyethylene, polyphenylsulfone, polysulfone, polythermide, acetal copolymer, polyester woven or solid or implantable grade lennite UHME-PE or other suitable implant material. In other embodiments, top exterior surface 165 and bottom exterior surface 166 can be can be composed of naturally occurring materials, such as an allograft bone tissue used for implantation within a mammal.

At least some of the above-referenced components and/or devices of system 100 (shown in FIG. 1) enable a modification to at least a portion of material substrate 102. For example, as shown in FIGS. 3A and 3B, the modification can include a pattern 310 on top surface 165 having dimensions and includes two or more discrete material alterations or changes spatially overlapped within the pattern. The modification can also include patterns that are discretely spaced or separated to create specific functionalities and have variable chemical and physical properties. That is, system 100 is configured for heterogeneous multi-material processing and for the expression of multiple functionalities on material substrate 102. In some embodiments, the design patterns can be, for example, electrically conductive pathways or networks 313 on top exterior surface 165. In some embodiments, the modifications or design patterns can also be made on at least a portion of bottom exterior surface 166, side exterior surface 167, and/or interior surface 309. In some embodiments, the modifications or design patterns can be made in at least a portion of the material (not shown) between top exterior surface 165 and bottom exterior surface 166. In some embodiments, portions of material substrate 102 can be transformed or modified into electrically conductive pathways 315 and the remaining portions of material substrate 102 that are not in the pathways 315 can remain unaltered.

In some embodiments, networks 313 and pathways 315 are designed and configured to interact with, for example, the body's cellular networks to best suit implant form and function. In some embodiments, networks 313 and pathways 315 can be intelligent micro- and nanoelectrical tapestries that can respond to physiological events at, for example, an implant site and orchestrate cell activity for optimum healing. The electrical networks and pathways can be patterned as, for example, electromechanically-active regions, such as piezoelectric and ferroelectric domains, that respond acutely to the mechanical forces experienced during normal physical activity. The mechanical perturbations and loading experienced by the electromechanically-active regions cause distinct electrical impulses to be created at the implant interface, which can enhance tissue growth and bone fusion by guiding bone cell proliferation and differentiation of osteogenic lineage and/or by mitigating stress shielding, bone loss and resorption. In another embodiment, the electrical networks and pathways can be patterned as electric field gradients that include, for example, electric charge distribution, electric field variation, and capacitively-coupled field charges. The electroactive regions can control and accentuate phenotype differentiation in stem cells, stimulate blood flow, and reduce pain and inflammation.

Figure 4:
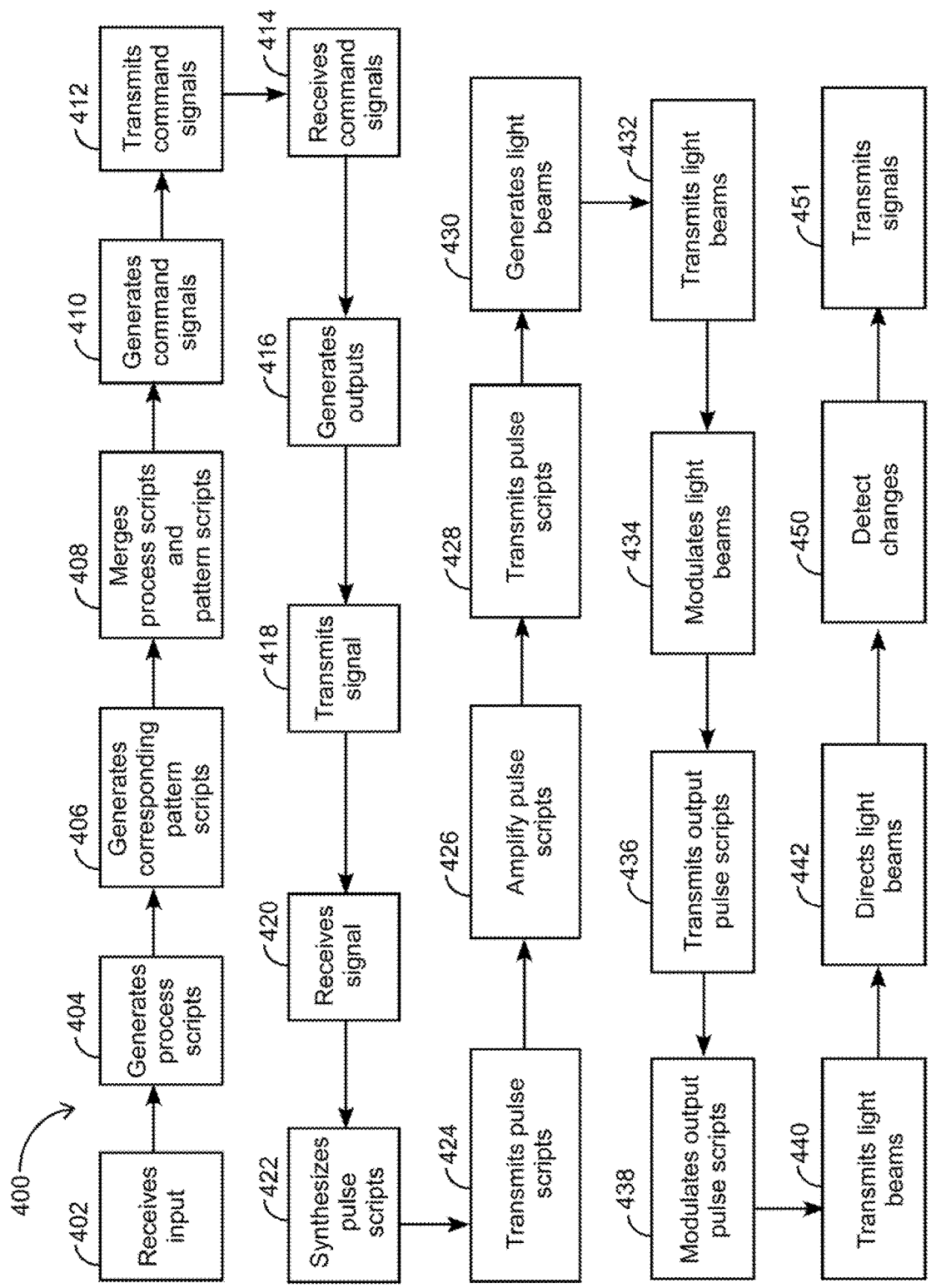
FIG. 4 is a flow diagram of an exemplary method that can be used for a modification of the material substrate using the system shown in FIG. 1, in accordance with some embodiments of the present disclosure.

FIG. 4 is a flow diagram 400 of an exemplary method for modifying a material substrate, such as material substrate 102 (shown in FIGS. 1, 3A, and 3B), using system 100 (shown in FIG. 1). In step 402, computing device 106 (shown in FIG. 1) receives an input from a user to modify material substrate 102. In some embodiments, the desired modification can be creating design patterns, such as conductive pathways 313 (shown in FIGS. 3A and 3B), on at least a portion of top exterior surface 165 (shown in FIGS. 1, 3A, and 3B) pursuant to various different desired parameters for pathways 313, such as desired dimensions and/or desired chemical and/or physical properties. In some embodiments, the desired modifications or design patterns can also be for the bottom exterior surface 166 (shown in FIGS. 1 and 3A), side exterior surface 167 (shown in FIGS. 1 and 3A), and/or interior surface 309 (shown in FIG. 3A) of material surface 102.

Based on the input, in step 404, computing device 106 generates one or more process scripts. In step 406, computing device 106 generates one or more pattern scripts that correspond to the process scripts. In some embodiments, the process scripts include different or discrete genotype pulse scripts or sequences, wherein each of the individual pulse sequences are based on nascent material properties of material substrate 102 and are designed to elaborate or express specific modifications in material substrate 102. The corresponding pattern scripts, in some embodiments, represent the laser machining code and contain the three-dimensional (3D) (or beyond) Cartesian coordinate information for the tool path geometry.

In some embodiments, the pulse scripts can be tailored and designed to elicit a diverse array of material modifications and inductions from the macroscale to the nanoscale. Such material modification and inductions include, but are not limited to, physical effects, such as patterning, structuring, texturing, morphology and topography, compaction and densification, mechanical strength and compliance. Chemical effects are also included, such as phase, composition and stoichiometry, ferroelectric, pyroelectric and piezoelectric behavior, magnetic induction and electrical conductivity.

In step 408, computing device 106 merges the process script(s) with the pulse script(s). For example, in some embodiments, the process script(s) are merged synchronously with the corresponding pulse script(s). Computing device 106, in some embodiments, is enabled to generate the process and pulse scripts and conduct the merging by being configured or having a processor, such as processor 230 (shown in FIG. 2), be programmed to enable the synchronized delivery of laser pulse sequences or photon exposure doses to material substrate 102 during patterning. For example, computer-assisted design (CAD) and manufacturing (CAM) software can be used that defines 3D pattern geometry and tool path motion and enables the user to select the type and spatial location of the material modification. In some embodiments, such software can be enhanced or modified to enable the line-by-line linking of the laser processing parameters to the motion control code, which facilitates communication between computing device 106 and other components and/or devices of system 100 for position-synchronized administration of prescribed laser pulse sequences.

In step 410, for example, computing device 106, generates a plurality of command signals that are based on the merged process and pattern scripts. In step 412, computing device 106 transmits the generated command signals to other components and/or devices of system 100. In some embodiments, the command signals can be transmitted simultaneously to each of the other components. Alternatively, in other embodiments, the command signals can be transmitted in a sequential order, such as numerical order, to the other components. In some embodiments, the command signals are representative of the various functions that each of the other components are to perform to ensure the desired modification is performed onto material substrate 102 based on the merged pattern script(s) and the process script(s). For example, the command signals can be representative of various functions that each of the other components are to perform to facilitate a modification that includes a pattern on at least a portion of a surface, such as top exterior surface 165, of material substrate 102. The modification can also include patterns that are discretely spaced or separated (as shown in FIGS. 3A and 3B) to create specific functionalities and have variable chemical and physical properties.

For example, in step 414, motion control apparatus 108 (shown in FIG. 1) receives at least one of the command signals. In some embodiments, motion control drive 110 (shown in FIG. 1) receives the signal and, in step 416, motion control drive 110 translates at least a portion of a sample of material substrate 102 into a 3D coordinate system, such as a 3D x-y-z Cartesian coordinate system. In some embodiments, the sample of material substrate 102 is positioned within a holder (not shown) of motion control drive 110.

In step 416, motion control drive 110 generates at least one output that provides instructions for the type of the plurality of pulse scripts to use for the modification to material substrate 102, wherein the instructions are based on the command signal that is received. For example, in some embodiments, the instructions can be instructions on how to modulate the pulse scripts for the intended modification. In step 418, motion control drive 110 transmits a signal representative of the output to waveform generator 124 (shown in FIG. 1) via second synch circuit 120 (shown in FIG. 1). In some embodiments, second synch circuit 120 facilitates transmitting the signals based on the command signals that it receives directly from computing device 106.

In step 420, waveform generator 124 receives the signal representative of the output. In step 422, waveform generator 124 synthesizes the pulse scripts based on the output. In some embodiments, such as in step 424, the newly synthesized pulse scripts are transmitted to amplifier 136 (shown in FIG. 1). In step 426, the transmitted pulse scripts are then amplified via amplifier 136. The newly synthesized and amplified pulse scripts are then transmitted to first EO modulator cell 142 (shown in FIG. 1) in step 428.

In step 430, laser 130 (shown in FIG. 1) generates a plurality of light beams based on signals received from master oscillator delay generator 126 (shown in FIG. 1). In some embodiments, master oscillator delay generator 126 facilitates the generation of the light beams based on command signals received directly from computing device 106.

In step 432, laser 130 transmits the light beams to first EO modulator cell 142. In step 434, first EO modulator cell 142 modulates the light beams from laser 130 to create the output pulse scripts pursuant to the desired modification (i.e., based on the command signals received from computing device 106). In some embodiments, synch circuit 120 facilitates the timing of the transmission of the amplified pulse scripts (step 424) and light beams (step 432) to first EO modulator cell 142 to ensure synchronization of the modulated pulse script delivery to the desired location on the material substrate 102.

After receiving the pulse scripts and the light beams, first EO modulator cell 142 transmits the output pulse scripts and newly modulated light beams to second EO modulator cell 144 (shown in FIG. 1) in step 436. After receiving the output pulse scripts and modulated light beams from first EO modulator cell 142, second EO modulator cell 144 further modulates the output pulse scripts and light beams pursuant to the desired modification in step 438 (i.e., based on the command signals received from computing device 106, and/or motion control apparatus 108, and/or waveform generator 124). In some embodiments, the newly synthesized pulse scripts can be transmitted to amplifier 140 (shown in FIG. 1), similar to step 426. The transmitted pulse scripts are then amplified via amplifier 140, similar to step 428. The newly synthesized and amplified pulse scripts are then transmitted to second EO modulator cell 144 (shown in FIG. 1). In some embodiments, this further modulation changes the polarization of the light beams. Accordingly, in steps 436 to 438, the pulse scripts can be modulated, for example, in amplitude (intensity), pulse duration (pulse width), frequency (repetition rate), spatial profile (energy distribution) and/or polarization (electric-field orientation), or any combination thereof to facilitate the changes of the light beams, which may be needed to achieve the desired modification. In some embodiments, synch circuit 120 facilitates the timing of the transmission of the amplified pulse scripts and light beams (steps 432) to second EO modulator cell 144 to ensure synchronization of the modulated pulse script delivery to the desired location on the material substrate 102.

In step 440, second EO modulator cell 144 transmits the light beams combined with the further modulated output pulse scripts to optical assembly 160 (shown in FIG. 1). In step 442, optical assembly 160 directs the light beams onto material substrate 102, such as, for example, at least a portion of top exterior surface 165 of material substrate 102 to create the modification onto at least the portion of surface 165 such that the modification includes a pattern on at least a surface of material substrate 102. The modification can also include patterns that are discretely spaced or separated to create specific functionalities and have variable chemical and physical properties. In another embodiment, optical assembly 160 can direct the light beams onto other portions of material substrate 102, such as bottom exterior surface 166, side exterior surface 167, and/or interior surface 309 to facilitate the same modification.

In some embodiments, the modification being done to material substrate 102 can be monitored in real-time. For example, in step 450, spectrometer 116 (shown in FIG. 2) can detect the changes being made to material substrate 102, such as detecting the various chemical and physical property changes to material substrate 102. In step 451, spectrometer 116 transmits a signal representative of the detected changes to computing device 102. After receiving the detected changes, computing device 106 determines whether the detected changes are consistent with the desired modification that was requested by the user. If the detected changes are deemed consistent, then computing device 106 lets the method continue. If, however, the detected changes are not deemed consistent, then computing device 106 generates one or more updated pattern scripts and one or more updated process scripts, and these updated pattern scripts and process scripts are used for the process as steps 404 to 451 are repeated until the desired modification is created on material substrate 102.

Based on the foregoing, waveform generator 124 enables the creation of a plurality of voltage scripts that can be used for the customization of the light beams that are used. Moreover, motion control apparatus 108 enables controlling the delivery and/or spatial location of each of the pulse sequences. As such, intercommunication link between, for example, modulator cells 142 and 144 and motion control apparatus 108 is based on a series of signal pulses generated from motion stage encoders (not shown) that delineate the progression of predefined distance along the 3D tool path pattern.

In some embodiments, the line-by-line matching of the process script and the pattern script is similar to DNA base-pairing in molecular biology, permitting the delivery of discrete pre-defined laser pulse scripts to material substrate 102 on a per-spot basis with resolution below the diffraction limit of light. In some embodiments, the pulse scripts are configured to activate or alter material substrate's 102 native character. For example, material substrate 102 can be transformed to a specific phase or disposition based on the underlying and predetermined fundamental solid state physics and photochemistry. The final state of material substrate 102 can be controlled by thermal and nonthermal channels and realized through chemical pathways or physical pathways. From a single laser process script, which comprises individual genotype pulse scripts, multiple material substrate states and functionalities with high resolution can be defined.

The individual pulse scripts can be based on the underlying chemical physics, solid state dynamics and photochemistry associated with the interactions between laser 130 and material substrate 102. The respective pulses in a sequence or script can be modulated in amplitude (intensity), pulse duration (pulse width), frequency (repetition rate), spatial profile (energy distribution) and polarization (electric-field orientation), or any combination thereof. In some embodiments, the pulse scripts are administered on a spot-by-spot basis, ensuring that each 3D pattern element or voxel receives the prescribed photon sequencing for the desired chemical or physical effect. The pulse scripts can be tailored and designed to elicit a diverse array of material substrate modifications and inductions from the macroscale to the nanoscale.

In some embodiments, materials, such as material substrate 102, can be guided into discrete phases and physical dispositions so that electromechanical behavior is attained. Laser pulse-scripted processing, as described in diagram 400, enables the careful regulation of energy flow into the material system, enabling thermal and nonthermal channels to be accessed for defining the processing mechanisms and the final material state. The laser pulse sequences within a pulse script can be specially devised to account for incubation effects and other time-dependent phenomena associated with the continuous evolution in the material's properties as a result of the laser exposure. For example, changes in morphology and roughness can impact absorptivity and surface reflectivity, and alterations in composition and phase can affect heat capacity, thermal conductivity and diffusivity. The pulse sequencing can accommodate the material dynamics, enabling the controlled delivery of energy into the material system for achieving the desired phase outcome with spatially overlapped structural and chemical modifications.

The ability to induce patterned, site-selective phase transformation and electromechanical activation in biomaterial systems enables implants and devices to actively respond to the body's natural mechanics. The embodiments described herein target the preparation of ferro-, piezo- and pyre-electric domains that are aligned with the form and function of the implant architecture. By imparting ferroelectric character into the material, any change in the lattice structure or geometry causes a change in the spontaneous polarization, resulting in a change in surface charge and the generation of current flow. The creation of a ferroelectric capacitor and the in situ generation of current occur without external voltage across a capacitor, enabling the fabrication of a mechanically-responsive device that can regulate local cell activity such as electrically induced osteogenesis. Two stimuli that can alter the lattice dimensions of a material substrate, such as substrate 102, are force and temperature. The generation of a surface charge and electrical current in response to the application of an external stress to a material is called piezoelectricity. A change in the spontaneous polarization of a material in response to a change in temperature is called pyroelectricity. General human activities can provide abundant dynamic forces and temperature variations at the implant location.

The embodiments described herein enable implants, for example, to be pre-programmed with electromechanical behavior, where the laser-activated domains can be structured from the macroscale to the nanoscale and designed to best suit cell functions and patient needs. The ferro-, piezo- and pyre-electrical character can be precisely aligned with the biomimetic geometry and superimposed on the architecture of the implant or interbody device. The spatial coupling provides unprecedented functional capability by combining electromechanical inductions (cell stimulation through electrical channels) with the patterned instruction of the biogeometric, microstructures and nanotopography (cell stimulation through physics). In some embodiments, the electromechanical structures can be tailored, on a site-selective basis, to interact and respond to the forces, pressures and loading experienced by the implant and surrounding regions during all phases of physiological activity. The implant can, in some embodiments, be designed to provide myriad electrical responses to the mechanical perturbations, enabling the creation of a multi-functional interbody device capable of controlling a diverse array of cellular mechanisms, like guiding proliferation and differentiation of osteogenic lineage or mitigating stress shielding, bone loss and resorption.

Exemplary embodiments of the systems and methods are described above in detail. The systems and methods are not limited to the specific embodiments described herein, but rather, components of the systems and/or steps of the method may be utilized independently and separately from other components and/or steps described herein. For example, the system may also be used in combination with other systems and methods, and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for modifying at least one material substrate, said system comprising:
    a computing device configured to:
        generate at least one process script for a modification to the at least one material substrate,
        generate at least one pattern script that corresponds to the at least one process script, for the modification to the at least one material substrate;
        merge the generated at least one process script with the corresponding generated at least one pattern script;
        generate a plurality of command signals that are based on the merged generated at least one process script and the corresponding generated at least one pattern script;
    an energy source configured to couple to said computing device, wherein said energy source is further configured to generate a plurality of light beams based on at least one of the generated plurality of command signals;
    at least one modulating component configured to couple to said computing device and said energy source, wherein said at least one modulating component is further configured to modulate the generated plurality of light beams based on at least one of the generated plurality of command signals;
    a waveform apparatus configured to couple to said computing device, said energy source, and said at least one modulating component, wherein said waveform apparatus is further configured to generate at least one waveform signal to customize the generated plurality of light beams based on at least one of the generated plurality of command signals; and
    a motion control apparatus that is configured to couple to said computing device, said at least one modulating component, said energy source, and said waveform apparatus, wherein said motion control apparatus is further configured to control at least one parameter of the plurality of light beams based on at least one of the generated plurality of command signals;
    wherein the generated at least one waveform signal enables the creation of a plurality of voltage scripts for the customization of the generated plurality of light beams.

2. A system in accordance with claim 1, wherein the generated at least one process script includes a plurality of different pulse sequences that are based, at least in part, on at least one property of the at least one material substrate.

3. A system in accordance with claim 2, wherein the plurality of different pulse sequences are configured to provide at least one modification to the at least one material substrate.

4. A system in accordance with claim 2, wherein said motion control apparatus is configured to control the at least one parameter of the plurality of light beams by being configured to control at least one of a delivery and a spatial location of each of the plurality of different pulse sequences.

5. A system in accordance with claim 1, wherein the corresponding generated at least one pattern script is representative of a laser machining code for the modification to the at least one material substrate.

6. A system in accordance with claim 1, wherein the corresponding generated at least one pattern script includes at least a three-dimensional Cartesian coordinate data for the modification to the at least one material substrate.

7. A method for modifying at least one material substrate, said method comprising:
    generating at least one process script, via a computing device, to modify the at least one material substrate;
    generating at least one pattern script that corresponds to the at least one process script, via the computing device, to modify the at least one material substrate;
    merging the generated at least one process script with the corresponding generated at least one pattern script;
    generating a plurality of command signals that are based on the merged generated at least one process script and the corresponding generated at least one pattern script;
    generating a plurality of light beams, via an energy source, based on at least one of the plurality of command signals;
    modulating the generated plurality of light beams, via a modulating component, based on at least one of the plurality of command signals;
    generating at least one waveform signal to customize the generated plurality of light beams, via a waveform apparatus, based on at least one of the plurality of command signals;
    controlling at least one parameter of the plurality of light beams, via a motion control apparatus, based on at least one of the plurality of command signals; and
    generating at least one waveform signal that enables the creation of a plurality of voltage scripts for the customization of the generated plurality of light beams.

8. A method in accordance with claim 7, wherein generating at least one process script further comprised generating a plurality of different pulse sequences that are based, at least in part, on at least one property of the at least one material substrate.

9. A method in accordance with claim 8, wherein generating a plurality of different pulse sequences comprises generating a plurality of different pulse sequences that are configured to provide at least one modification to the at least one material substrate.

10. A method in accordance with claim 8, wherein controlling at least one parameter of the plurality of light beams further comprises controlling at least one of a delivery and a spatial location of each of the plurality of different pulse sequences.

11. A method in accordance with claim 7, wherein generating at least one pattern script further comprises generating at least one pattern script that is representative of a laser machining code for the modification to the at least one material substrate.

12. A method in accordance with claim 7, wherein generating at least one pattern script further comprises generating at least one pattern script that includes at least a three-dimensional Cartesian coordinate data for the modification to the at least one material substrate.

13. A system comprising:
at least one material substrate;
a computing device positioned proximate to said at least one material substrate, said computing device is configured to:
   generate at least one process script for a modification to at least a surface of said at least one material substrate,
   generate at least one pattern script that corresponds to the at least one process script, for the modification to at least the surface of said at least one material substrate;
   merge the generated at least one process script with the corresponding generated at least one pattern script;
   generate a plurality of command signals that are based on the merged generated at least one process script and the corresponding generated at least one pattern script;
an energy source configured to couple to said computing device, wherein said energy source is further configured to generate a plurality of light beams based on at least one of the generated plurality of command signals;
at least one modulating component configured to couple to said computing device and said energy source, wherein said at least one modulating component is further configured to modulate the generated plurality of light beams based on at least one of the generated plurality of command signals;
a waveform apparatus configured to couple to said computing device, said energy source, and said at least one modulating component, wherein said waveform apparatus is further configured to generate at least one waveform signal to customize the generated plurality of light beams based on at least one of the generated plurality of command signals; and
a motion control apparatus that is configured to couple to said computing device, said at least one modulating component, said energy source, and said waveform apparatus, wherein said motion control apparatus is further configured to control at least one parameter of the plurality of light beams based on at least one of the generated plurality of command signals; and
wherein the generated at least one waveform signal enables the creation of a plurality of voltage scripts for the customization of the generated plurality of light beams.

14. A system in accordance with claim 13, wherein the generated at least one process script includes a plurality of different pulse sequences that are based, at least in part, on at least one property of said at least one material substrate.

15. A system in accordance with claim 14, wherein the plurality of different pulse sequences are configured to provide at least one modification to at least a surface of said at least one material substrate.

16. A system in accordance with claim 14, wherein said motion control apparatus is configured to control the at least one parameter of the plurality of light beams by being configured to control at least one of a delivery and a spatial location of each of the plurality of different pulse sequences.

17. A system in accordance with claim 13, wherein the corresponding generated at least one pattern script is representative of a laser machining code for the modification to at least the surface of said at least one material substrate and the corresponding generated at least one pattern script includes at least a three-dimensional Cartesian coordinate data for the modification to said at least one material substrate.

* * * * *